United States Patent [19]

Meyer

[11] Patent Number: 5,105,489
[45] Date of Patent: Apr. 21, 1992

[54] DEVICE AND METHODOLOGY FOR CORRECTING SCOLIOSIS

[76] Inventor: Donald Meyer, 20272 Lantana, Huntington Beach, Calif. 92646

[21] Appl. No.: 637,068

[22] Filed: Jan. 3, 1991

[51] Int. Cl.$^5$ .......................... A47C 7/00; A61H 1/00
[52] U.S. Cl. ................................ 5/652; 5/448; 297/458
[58] Field of Search ............. 5/431, 438, 437, 442, 5/446, 448; 128/68, 69, 70; 297/458, 459

[56] References Cited

U.S. PATENT DOCUMENTS

| | | | |
|---|---|---|---|
| 3,763,509 | 10/1973 | Mittendorf | 5/442 |
| 3,775,785 | 12/1973 | Mittendorf | 5/465 X |
| 3,815,586 | 6/1974 | Kazik | 128/70 |
| 4,653,622 | 6/1987 | Berube | 128/68 |
| 4,824,169 | 4/1989 | Jarrell | 297/458 X |

Primary Examiner—Michael F. Trettel
Attorney, Agent, or Firm—Spensley Horn Jubas & Lubitz

[57] ABSTRACT

A device and method for treating scoliosis utilizing an easy to use seat cushion comprised of two members having angled top surfaces. The two members are arranged in an opposed side-by-side position. In use, the innominate bones and entire pelvic girdle of a patient seated on the seat cushion are tractioned into an opposing configuration through application of torque thereto and tilting thereof.

20 Claims, 1 Drawing Sheet

DEVICE AND METHODOLOGY FOR CORRECTING SCOLIOSIS

BACKGROUND OF THE INVENTION

1. Field of the Invention

The present invention relates generally to devices and methods for correcting spinal and pelvic abnormalities, and more particularly to a device and method for correcting non-structural scoliosis.

2. Related Art

Non-structural scoliosis is defined as a lateral curvature of the spine not associated with a structural alteration of the spine. Such aberrant curvatures of the spine not only disfigure a person but may also be associated with severe pain.

Most currently accepted methods of treatment of scoliosis focus on the spine. In an attempt to halt the progression of scoliosis, physical electro-therapy, spinal manipulation and/or thoraco-lumbar exercises may be prescribed to stimulate, strengthen and mobilize the spine. Additionally, treatments of progressive or moderate to severe scoliosis typically include utilization of a brace ("Milwaukee Brace") which must oftentimes be worn for 23 to 24 hours a day.

While all of these treatments have shown some success in temporarily halting or reversing scoliosis, none have been able to produce any long-term correction of this condition. It is the inventor's belief that the main reason for this treatment failure lies in the fact that these therapies are aimed at the spinal curvature itself and not the true etiologic agent of the condition, the pelvis.

It has been determined through x-ray study that aberrant lateral curvatures of the spine can result from aberrant postures of flexion and extension of the innominate bones of the pelvis ("pelvic torque") with associated compensatory rotation of the entire pelvic girdle. Additionally, the pelvis may also be held in an aberrant position of either right or left lateral flexion ("pelvic tilt"). This lateral flexion of the pelvic girdle produces a compensatory opposite lateral-rotary motion into the lumbar or thoraco-lumbar spine, i.e., the laterally flexed spine rotates about its longitudinal axis in the opposite direction of lateral flexion. It is the combination of these aberrant pelvic postures that is believed to produce the various forms of lumbar or thoraco-lumbar scoliosis, as well as any compensatory thoracic or cervico-thoracic spinal changes by altering the associated connective tissue.

To be effective, a treatment regime must therefore affect the altered bio-mechanics of the pelvis and the thoraco-lumbar spine simultaneously. One effective treatment for certain types of scoliosis is the utilization of a heel lift, worn on the side of the scoliotic curvature. Unfortunately, this treatment has several shortcomings. First, it may only be utilized with those altered pelvic configurations producing a certain pelvic torque, i.e., which may be counteracted by the influence of the heel lift to the right or left innominate bone. Additionally, the heel lift affects the altered bio-mechanics of the innominate bones to a much larger degree than the altered bio-mechanics of the spine. Finally, this treatment is only effective while the patient is standing. As the patient sits down, the pelvis and especially the thoraco-lumbar spine are again being subjected to the same altered bio-mechanical connective tissue stresses, usually to a more severe degree than the standing posture.

It would be desirable to have an effective treatment regime which can accomplish correction of both pelvic torque and pelvic tilt associated with scoliosis and which may be utilized in the seated position. The present invention provides such a treatment.

SUMMARY OF THE DISCLOSURE

Embodiments of the present invention comprise a seat cushion and a method for its use to facilitate the reversal of non-structural scoliosis and other conditions caused by aberrant positions of the pelvic girdle. When sat upon by a patient, the seat cushion of an embodiment of the invention functions to traction an opposing abberant position of the innominate bones of the patient's pelvis and the entire pelvic girdle to counteract both pelvic torque and pelvic tilt.

A preferred embodiment of the seat cushion comprises at least two angled members positioned in an opposing side-by-side arrangement. In a preferred embodiment, the two angled members comprise triangular solids or wedges connected in their opposing side-by-side arrangement.

DESCRIPTION OF THE DRAWINGS

Like reference characters in the various drawings refer to like elements.

DETAILED DESCRIPTION OF THE PREFERRED EMBODIMENTS

The following description is of the best presently contemplated mode of carrying out embodiments of the invention. This description is made for the purpose of illustrating the general principles of the invention and should not be taken in a limiting sense. The scope of the invention is best determined by reference to the appended claims.

Figure 1:
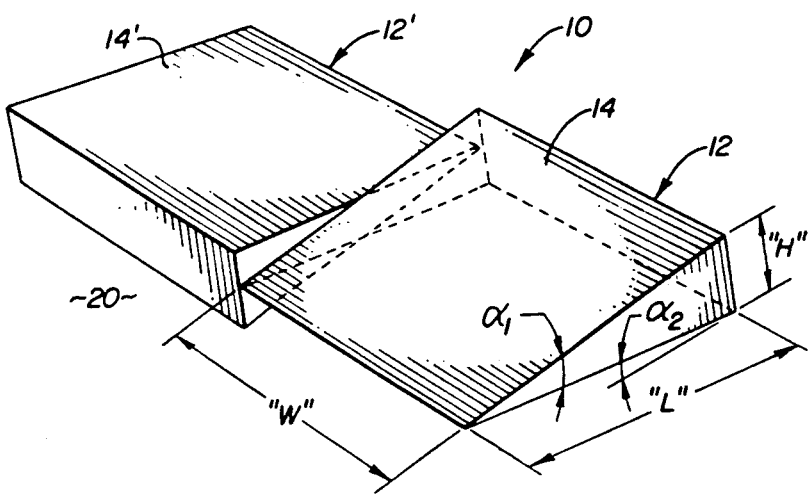
FIG. 1 is a perspective view of a preferred embodiment of a seat cushion according to the present invention.

FIG. 1 shows a perspective view of a preferred embodiment of a seat cushion 10 according to the present invention. The seat cushion 10 includes two identical triangular solid members 12 and 12' connected in an opposing side-by-side arrangement. Each of the triangular solid members 12, 12' includes an angled top surface 14, 14' for engaging the right and left buttock of a person using the device, respectively.

Each of the triangular solid members 12, 12' has a length "L" preferably ranging from 10.5" to 12.5"; a width "W" preferably ranging from 13" to 15"; a height "H" preferably ranging from 2.75" to 3.25"; and an angle of inclination $\alpha_1$ preferably ranging from 13° to 17°, optimally being approximately 15°. The two triangular solid members 12, 12' are preferably connected in side-by-side alignment along their lengths L so that when the device 10 is placed on a flat surface, each triangular solid member 12, 12' has an angle of elevation $\alpha_2$ preferably ranging from 6.5° to 8.5°, optimally being approximately 7.5°. The connection may be made by adhesive, blind doweling, or other mechanical means, or the two triangular solid members 12, 12' can be molded or manufactured as an integral unit.

For a small person, medium person and large or overweight person, the cushion may optimally be formed as in Table I.

TABLE 1

| | WEIGHT | L | W | H | L₁ | L₂ |
|---|---|---|---|---|---|---|
| SMALL BODY FRAME | 50 LB-110 LB | 10¼" | 13" | 2¾" | 15° | 7¼° |
| MEDIUM BODY FRAME | 110 LB-175 LB | 11¼" | 14" | 3" | 15° | 7¼° |
| LARGE BODY FRAME | 175 LB-+ | 12¼" | 15" | 3¼" | 15° | 7¼° |

The device 10 is preferably made of a closed cell, polyethylene foam having a density (PCF) of 1.9, tensile strength (PSI) of 50, elongation % of 180, tear strength (lbs/inch) of 10.2, compression resistance (deflection) (PSI 25% comp) of 7.8 and compression set (50%) (% original thickness) of 12. Such material is available from Industrial Rubber & Supply, Inc. of Tacoma, Wash. under the trademark Sentinel Microcell ®. Other materials, including non-pliant materials, can be used so long as the material provides the desired support, while affording a comfortable degree of cushioning to the user.

Figure 3:
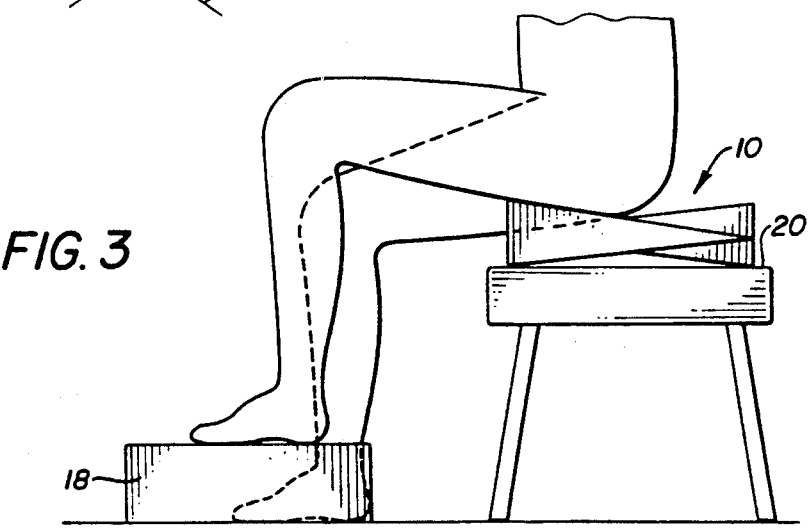
FIG. 3 is a perspective view of the device of FIG. 1 in use.

FIG. 3 depicts the seat cushion 10 in use. The seat cushion 10 is placed on a flat, preferably firm surface 20 and the patient is seated thereon with the right buttock supported by the top surface 14 of the triangular solid member 12 and the left buttock supported by the top surface 14' of triangular solid member 12'. The person can also use the cushion so that the right buttock is supported by the top surface 16' of the triangular solid member 12' and the left buttock supported by the top surface 16 of triangular solid member 12.

Figure 2:
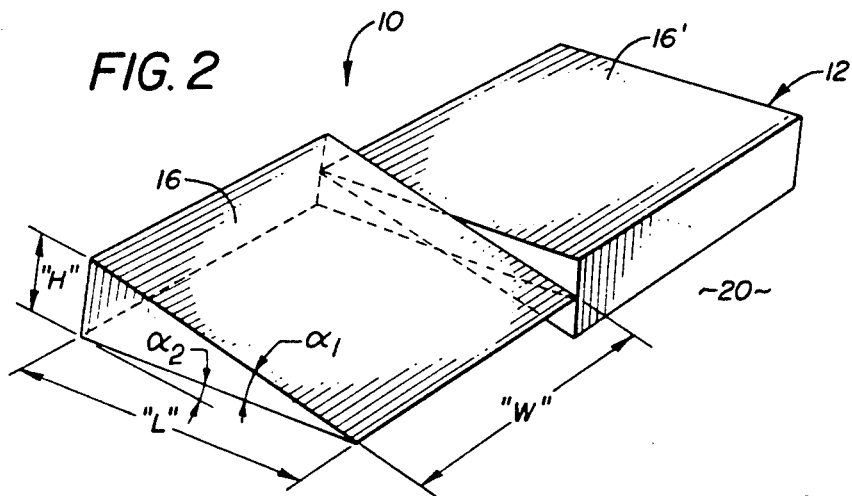
FIG. 2 is a perspective view of the seat cushion of FIG. 1, turned over.

The seat cushion 10 functions to correct all aberrant pelvic orientations. If the patient is suffering from an aberrant pelvic orientation whereby the right innominate bone is in a position of flexion and the left innominate bone is in a position of extension, and the patient has a right pelvic tilt, the patient will sit on the front portion of the cushion shown in FIG. 1 on side 14, 14'. If, however, the patient's right innominate bone is in a position of flexion and the left innominate bone is in a position of extension, and the patient has a left pelvic tilt, the patient should be instructed to sit on the rear portion of the seat cushion 10 on side 14, 14'. If the patient's right innominate bone is in a position of extension and the left innominate bone is in a position of flexion, and the patient has a right pelvic tilt, the patient will sit on the rear portion of the cushion in FIG. 2 on side 16, 16'. If the patient's innominate bones are in the same torqued malposition as just described but has a left pelvic tilt, the patient should be instructed to use the front portion of the cushion on side 16, 16'.

Used as described, the triangular solid members 12, 12' apply opposing torque to the innominate bones and tilt the entire pelvic girdle to force extension of the flexed innominate bone and flexion of the extended innominate bone and force an opposing tilt or lateral flexion of the entire pelvic girdle to thereby force (or traction) it into an opposing configuration. This forced opposing configuration of the pelvis will induce an opposite configuration of the thoraco-lumbar spine and any compensatory changes of the cervico-thoracic spine by reversing the aberrant stresses on the associated paravertebral connective tissue and thereby re-educating those tissues. The scoliotic condition may thus be corrected or reversed over a period of time.

It should be appreciated that the actual dimensions of the cushion 10 will depend upon the size of the user. The dimensions will be created so that when sitting upon the seat cushion, the innominate bones and pelvic girdle will move as noted above.

The inventive seat cushion 10 is very effective in reversing scoliosis since the increased structural strain associated with the seated posture makes this position the most effective for traction of the thoracolumbar and lumbo-sacral paravertebral connective tissue. Furthermore, since the device is very easy and, after a period of acclimation, comfortable to use, patient compliance with the use instructions can be expected.

The effectiveness of the inventive seat cushion and method of use can be increased by utilization of a foot block 16 (see FIG. 3) or other support under the patient's foot on the side of the flexed innominate bone to further force extension thereof. Additionally, corrective lumbo-pelvic exercises may be performed by the patient while using the device 10. Such exercises preferably include:

1) Strong thoraco-lumbar rotations away from the P.I. innominate bone.
2) Strong thoraco-lumbar lateral flexions away from the scoliodic concavity.
3) Strong knee to chest pulls on the side of the flexed innominate bone.
4) Lumbar lordotic arch and hold, for a 8-10 count.

While a preferred embodiment of the inventive device comprises two identical connected triangular solid members 12, 12', other angled configurations capable of producing the desired realignment of the bones of the pelvis may be utilized. For example, wedge-shaped members constructed of variable density material or parallelogram-shaped members. Such alternately-shaped members need not necessarily be connected in their side-by-side arrangement but instead may simply be positioned in a side-by-side orientation for use. Alternatively, the inventive seat cushion may be manufactured as a single unit including the desired angled top surface.

One preferred embodiment of the present invention has been illustrated and described. Nevertheless, it will be understood that various modifications may be made without departing from the spirit and scope of the invention. Accordingly, it is to be understood that the invention is not to be limited by the specific illustrated embodiment, but only by the scope of the appended claims.

I claim:

1. A device for correcting scoliosis comprising at least two angled members, each angled member provided with an upper surface having a first end at a first vertical height and a second end at a second vertical height, the second vertical height being greater than the first vertical height, and a side surface extending from the upper surface from the first end to the second end, the angled members being positioned in angle-opposed side-by-side arrangement, wherein the side surface of each angled member is adjacent and facing the side surface of another angled member, with the first end of the upper surface of each angled member next to the second end of the upper surface of another angled member.

2. The device of claim 1, wherein the plurality of angled members numbers two.

3. The device of claim 2, wherein the two angled members are identical.

4. The device of claim 3, wherein the two angled members are connected in their opposed side-by-side arrangement.

5. The device of claim 1, wherein the angled members comprise triangular solids connected in lengthwise alignment.

6. A device for correcting scoliosis comprising at least two angled members in angle-opposed side-by-side arrangement, the angled members comprising triangular solids connected in lengthwise alignment, wherein each triangular solid has a length ranging from 10.5" to 12.5", a width ranging 13" to 15", and a height ranging from 2.75" to 3.25", and an angle of inclination ranging from 13° to 17°, and wherein the two triangular solids are connected so that when the device is placed on a flat surface, each triangular solid has an angle of elevation ranging from 6.5° to 8.5°.

7. The device of claim 6, wherein each triangular solid has a length of approximately 10.5 inches, a width of approximately 13 inches, a height of approximately 2.75 inches, an angle of inclination of approximately 15°, and an angle of elevation of approximately 7.5°.

8. The device of claim 6, wherein each triangular solid has a length of approximately 11.5 inches, a width of approximately 14 inches, a height of approximately 3 inches, an angle of inclination of approximately 15°, and an angle of elevation of approximately 7.5°.

9. The device of claim 6, wherein each triangular solid has a length of approximately 12.5 inches, a width of approximately 15 inches, a height of approximately 3.25 inches, an angle of inclination of approximately 15°, and an angle of elevation of approximately 7.5°.

10. A device of facilitating the correction of scoliosis comprising means for applying torque to innominate bones of the pelvis and simultaneously tilting the pelvis, wherein the means for applying torque and tilting comprises at least two members, each member including an angled top surface having a first end at a first vertical height and a second end at a second vertical height, the second vertical height being greater than the first vertical height, the angled top surface of each member for supporting one of the innominate bones of the pelvis and each member including a side surface extending from the angled top surface from the first end to the second end, and wherein the members are positioned with the side surface of each member adjacent and facing the side surface of another member and with the angled top surfaces of two adjacent members arranged in an angle opposing relationship to each other.

11. The device of claim 10, wherein the plurality of members numbers two and wherein each member is identical and configured in the shape of triangular solid.

12. The device of claim 11, wherein the triangular solids are connected along one of each of their sides.

13. A method for correcting scoliosis comprising the steps of:

providing a structure having an upper surface defining at least two angled surfaces, each angled surface having a first edge extending from a first vertical height to a second vertical height, the second vertical height being greater than the first vertical height, the first edge being positioned adjacent the first edge of another angled surface with the first vertical height portion of each angled surface being positioned adjacent the second vertical height portion of the adjacent angled surface; and applying torque to the innominate bones of a pelvis and tilting the pelvis while sitting on the upper surface of the structure.

14. The method of claim 13, wherein the structure comprises a plurality of angled members and the torque is applied to the innominate bones and the pelvis is tilted by the plurality of angled members having angled top surfaces for engaging the buttocks of a patient suffering from scoliosis when the patient is seated on the members.

15. The method of claim 14, wherein the plurality of members numbers two and the two members are arranged in an opposed side-by-side position.

16. The method of claim 13, further comprising the step of performing pelvic and thoraco-lumbar exercises while torque is applied to the innominate bones and the pelvis is being tilted.

17. The method of claim 13, further comprising the step of providing a support under at least one of the seated patient's feet.

18. A seat cushion comprising at least two angled members, each angled member provided with an upper surface having a first end at a first vertical height and a second end at a second vertical height, the second vertical height being greater than the first vertical height and a side surface extending from the upper surface from the first end to the second end, the angled members being positioned in angle-opposed side-by-side arrangement, where the side surface of each angled member is adjacent and facing the side surface of another angled member with the first end of the upper surface of each angled member next to the second end of the upper surface of another angled member.

19. A seat cushion comprising at least two angled members in angle-opposed side-by-side arrangement, the angled members comprise triangular solids connected in lengthwise alignment, wherein each triangular solid has a length ranging from 10.5" to 12.5", a width ranging from 13" to 15", and a height ranging from 2.75" to 3.25", and an angle of inclination ranging from 13° to 17°, and wherein the two triangular solids are connected so that when the device is placed on a flat surface, each triangular solid has an angle of elevation ranging from 6.5° to 8.5°.

20. A seat cushion comprising a cushion structure defining an upper surface having at least two angled surfaces, each angled surface having a first edge extending from a first end at a first vertical height to a second end at a second vertical height, the second vertical height being greater than the first vertical height, the first edge being positioned adjacent the first edge of another angled surface with the first vertical height end of each angled surface being positioned adjacent the second vertical height end of the adjacent angled surface.

* * * * *